US00PP17180P2

(12) United States Plant Patent
Jones

(10) Patent No.: US PP17,180 P2
(45) Date of Patent: Oct. 31, 2006

(54) ***DIASCIA* PLANT NAMED 'PENDER'**

(50) Latin Name: *Diascia×hybrida*
Varietal Denomination: PENDER

(76) Inventor: Sidney James Jones, 14 Avondale Road, Pontnewydd, Cwmbran, Wales, NP44 1UD (GB)

( * ) Notice: Subject to any disclaimer, the term of this patent is extended or adjusted under 35 U.S.C. 154(b) by 0 days.

(21) Appl. No.: 11/189,157

(22) Filed: Jul. 25, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Diascia* plant named 'PENDER' that is characterized by compact habit, green leaves, and flowers that are deep salmon-pink in color. In combination these traits set 'PENDER' apart from all other existing varieties of *Diascia* known to the inventor.

2 Drawing Sheets

Genus: *Diascia*. Species:×*hybrida*.
Denomination: 'PENDER'.

BACKGROUND OF THE INVENTION

The present invention relates to a new and distinct cultivar of twinspur, a perennial that is grown for use in raised beds, borders, hanging baskets, and patio containers. The new cultivar is known botanically as *Diascia* and will be referred to hereinafter by the cultivar name 'PENDER'.

The inventor has been interested and has collected plants of the genus *Diascia* since the early 1990s. *Diascia,* which is native to southern Africa, provides showy annual and perennial (in mild climates) plants whose predominant flower color range in nature is in the range of soft to dark pink, also white, lavender-pink, salmon and apricot. Plants of *Diascia* which are raised from seed are inherently variable in growth habit, ranging from loose, weak plants with brittle stems to plants with significantly shorter internodes resulting in more compact forms and therefore more dense flowering characteristics. Various breeding programs, including the inventor's , have aimed to develop improvements in plant habit and also an extension in the color range into deep pink or red or orange shades and ideally with very similar compact habits for each color.

In 1995, the inventor commenced a deliberate program to develop a range of *Diascias* whose characteristics would be common throughout, namely an extremely compact plant habit with bright flower colors, and in a range of colors. In 1995 the inventor selected from his collection several plants with the dwarfest habit and hand-pollinated amongst them. The plants involved in the hybridization are unknown although some were numbered selections from prior work.

The seedlings raised during 1995 flowered in the same year and many were retained for further observation in 1996 and 1997. In May 1997, the inventor determined that one plant, PENDAN (unpatented), exhibited exceptional characteristics of dense mounding habit and bright clear saturated pink flowers.

The new *Diascia,* PENDER was selected in summer of 2002 as a naturally occuring sport found by the inventor to be growing amongst a block of mother plants of PENDAN. The mother plants of PENDAN were all in flower and were growing in 5 liter containers in the inventor's greenhouse in Penhow, Newport, Wales, United Kingdom. Although PENDER exhibited the same overall habit and density of flowering as PENDAN, the inventor was able to distinguish PENDER by its significantly different deep salmon-pink flowers. The inventor considers that the combination of deep salmon-pink flowers and dense mounding habit sets PENDER apart from other cultivars of *Diascia* known to the inventor.

The distinguishing characteristics of 'PENDER' are compact habit, green leaves, and flowers that are deep salmon-pink in color. The flowers of 'PENDER' bloom profusely spring, summer, and fall. The parent *Diascia* 'PENDAN' is the closest comparison plant. The new *Diascia* cultivar 'PENDER' is distinguishable from the parent 'PENDAN' solely by flower colors which are deep salmon-pink and mid pink respectively. In all other traits the two plants are identical.

The first asexual propagation of the new *Diascia* cultivar 'PENDER' was conducted in 2003 by the inventor at his nursery in Newport, Gwent, England. The method of asexual propagation used was vegetative tip cuttings. Since that time the unique and distinguishing characteristics of 'PENDER' have been determined stable, fixed, and reproduce true to type in successive generations of asexual reproduction.

SUMMARY OF THE INVENTION

The following traits have been repeatedly observed and represent the characteristics of the new *Diascia* cultivar 'PENDER'. These traits in combination distinguish 'PENDER' from all other commercial varieties of *Diascia* known to the inventor. 'PENDER' has not been tested under all possible conditions and phenotypic differences may be observed with variations in environmental, climatic, and cultural conditions, without however, any difference in genotype.

1. 'PENDER' exhibits compact habit.
2. 'PENDER' exhibits flowers that are deep salmon-pink in color.
3. 'PENDER' blooms profusely spring, summer, and fall.
4. 'PENDER' exhibits green leaves.
5. 'PENDER' is propagated using the method of vegetative tip cuttings.
6. 'PENDER' is 25 cm. in height and 62 cm. in width in a 5 liter container.
7. The cultural requirements of 'PENDER' are well-draining soil, full sun, and regular water.
8. 'PENDER' is suitable for use in raised beds, borders, hanging baskets, and patio containers.
9. 'PENDER' is hardy to USDA Zone 7.

BRIEF SUMMARY OF THE DRAWINGS

The accompanying color drawings

Figure 1:
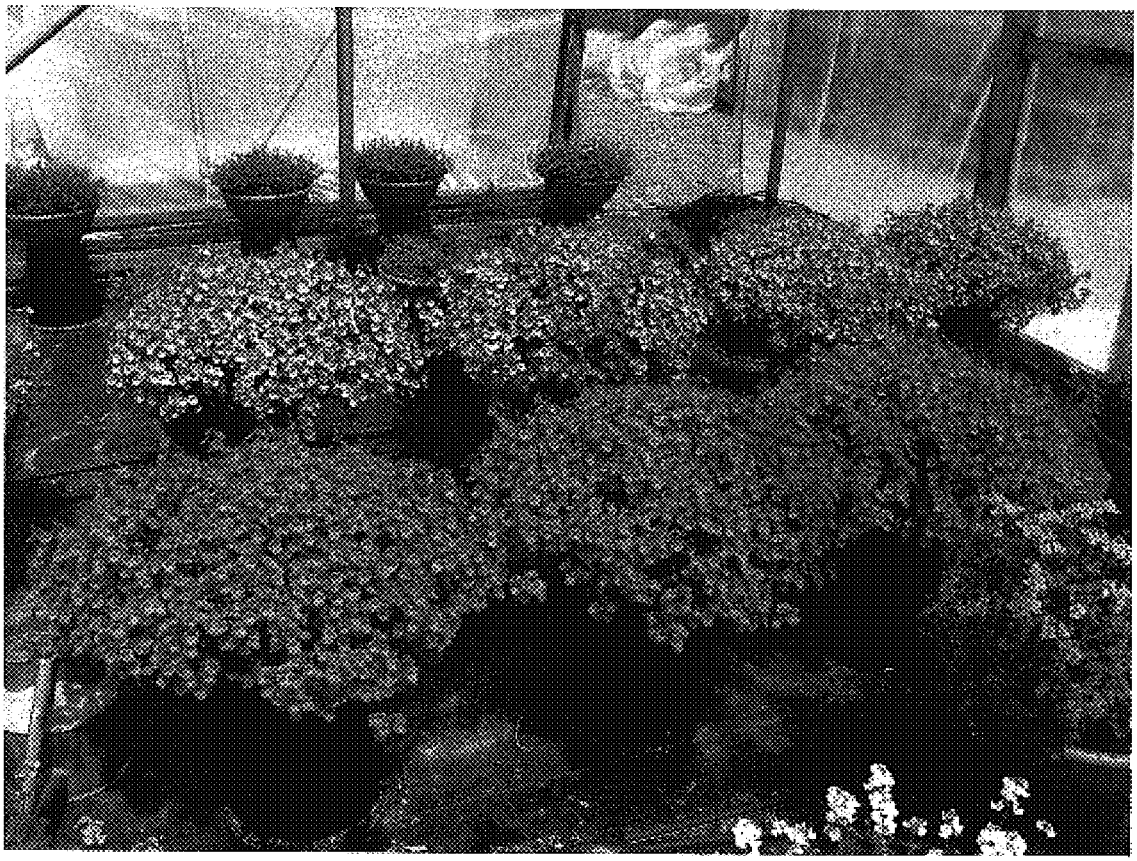
FIG. 1 and FIG. 2 illustrate the overall appearance of the new *Diascia* cultivar 'PENDER' showing colors as true as it is reasonably possible to obtain in colored reproductions of this type. Colors in FIG. 1 and FIG. 2 may differ from the color values cited in the detailed botanical description, which accurately describe the actual colors of the new variety of *Diascia* named 'PENDER'.

The drawing labeled as FIG. 1 depicts, in the foreground, three whole plants of 'PENDER' in full bloom illustrating habit and deep salmon-pink flower color. Behind the three plants of 'PENDER' are lined up four plants of the parent PENDAN'. This drawing illustrates the very similar habits of 'PENDER' and 'PENDAN' and the differing flower colors of deep salmon-pink and mid pink respectively. The illustrated plants have all been grown in 5 liter containers in the inventor's greenhouse in Newport, Wales, United Kingdom. The parts of plants with white and blue flowers which are present in the front right corner of the drawing are extraneous. The partially grown plants in the very background of the drawing are also extraneous.

Figure 2:
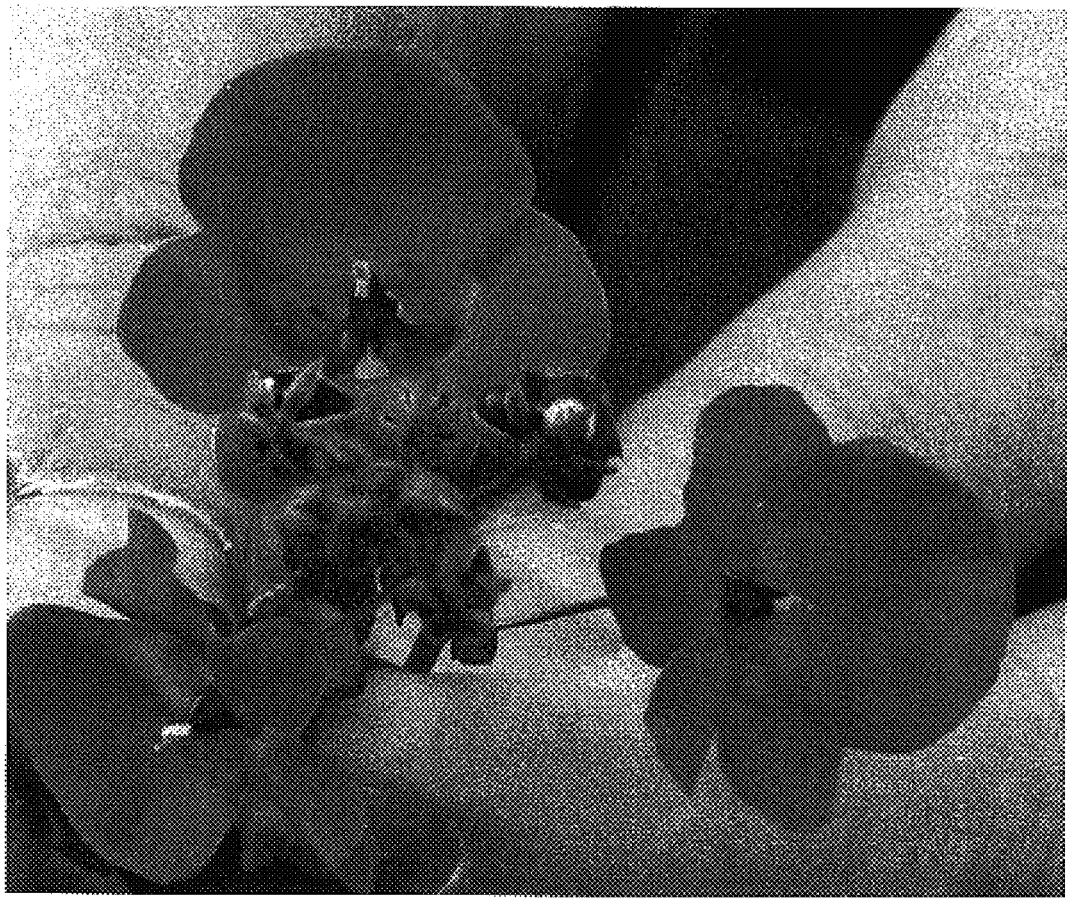

The drawing labeled as FIG. 2 illustrates a close up of a typical inflorescence of 'PENDER' and the characteristic deep salmon-pink of the flower color.

Both the drawings were made using conventional photographic techniques. Although colors may appear different from actual colors due to light reflectance, they are as accurate as possible by conventional photography.

BOTANICAL DESCRIPTION OF THE PLANT

The following is a detailed description of the new *Diascia* cultivar 'PENDER'. Data was collected June 2005 in Arroyo Grande, Calif. from 18 month old plants growing in 5 liter containers. The color determinations are in accordance with the 2001 edition of The Royal Horticultural Society Colour Chart, except where general color terms of ordinary dictionary significance are used. The new *Diascia* variety named 'PENDER' has not been observed under all possible environmental conditions. Phenotypic differences may be observed with variations in environmental, climatic, and cultural conditions, without however, any difference in genotype.

Botanical classification: *Diascia×hybrida* 'PENDER'.
Genus: *Diascia.*
Species:×*hybrida.*
Denomination: 'PENDER'.
Common name: Twinspur.
Commercial classification: Perennial.
Plant uses: Suitable for use in raised beds, borders, hanging baskets and patio containers.
Cultural requirements: Provide well-draining soil, full sun and regular water.
Hardiness: Hardy to USDA Zone 7.
Parentage: *Diascia* 'PENDER' was discovered as a naturally occurring branch mutation of the following parent:
*Parent plant.*—An individual whole plant of *Diascia* 'PENDAN'.
Plant description:
*Blooming seasons.*—Spring, summer and fall.
*Plant habit.*—Compact habit.
*Plant form.*—Mounding form.
*Plant vigor.*—Vigorous.
*Plant propagation method.*—Propagated using the method of vegetative tip cuttings.
*Plant height.*—Plant is 25 cm. in height in a 5 liter container.
*Plant width.*—Plant is 62 cm. in width in a 5 liter container.
*Number of flowers and buds per inflorescence.*—An average of 6 flowers and 6 buds are present on an individual inflorescence.
*Root system.*—Fine and fibrous roots.
*Resistance and susceptibility to diseases and pests.*—No resistance or susceptibility to pests or disease is known to the inventor.
*Crop time.*—3 months are needed to produce a finished 1-liter commercial container from a rooted cutting.
*Time to develop roots.*—10–14 days are needed to develop roots on an initial cutting.
*Special considerations.*—Encourage new branching by periodic pruning.
Stem, branches: The stem produces 3–4 branching stems at 1 cm. above the surface. Each branching stem produces 1–2 nodal sub-branches. Each sub-branch produces further nodal branching stems which flower at approximately 2 weeks after final pinch .
*Flowering stems per plant.*—Approximately 100.
*Stem shape.*—Stem is quadrilateral in shape.
*Stem color.*—Stem is 138B in color.
*Stem length.*—Stem is 1 cm. in length.
*Stem diameter.*—Stem is 4 mm. in diameter.
*Internode length.*—Internode ranges from 2 cm. to 4.50 cm. in length.
*Stem surface.*—Glabrous stem surface.
*Branching stem length at flowering.*—19 to 30 cm.
*Branching stem diameter.*—2 mm.
Foliage:
*Average number of leaves per branching stem.*—4–8.
*Leaf arrangement.*—Opposite.
*Leaf division.*—Simple.
*Leaf shape.*—Leaf is cordate in shape.
*Leaf base.*—Cordate base.
*Leaf apex.*—Acute apex.
*Leaf margin.*—Denticulate margin.
*Leaf venation pattern.*—Pinnate vein pattern.
*Vein color* (*abaxial surfaces*).—Vein is 138B in color.
*Vein color* (*adaxial surfaces*).—Vein is 137A in color.

*Leaf surface* (*abaxial surface*).—Glabrous leaf surface.
*Leaf surface* (*adaxial surface*).—Glabrous leaf surface.
*Leaf color* (*abaxial surface*).—Leaf is 138B in color.
*Leaf color* (*adaxial surface*).—Leaf is 137A in color.
*Leaf appearance* (*abaxial surface*).—Matte in appearance.
*Leaf appearance* (*adaxial surface*).—Matte in appearance.
*Leaf length.*—Leaves on an individual plant range from 1.25 cm. to 2.50 cm. in length.
*Leaf width.*—Leaves on an individual plant range from 1 cm. to 2 cm. in width.
*Leaf attachment.*—Petiolate.
*Petiole surface.*—Stipitate glandular petiole surface.
*Petiole dimensions.*—Petiole dimensions are 5 mm. in length and 2 mm. in diameter.
*Petiole shape.*—Sulcate in shape.
*Petiole color.*—Petiole is 138B in color.
*Leaf fragrance.*—No leaf fragrance is observed.

Flower:
*Inflorescence type.*—Terminal raceme.
*Inflorescence dimensions.*—4 cm. in depth and 5 cm. in diameter.
*Flower aspect.*—Flowers on an individual plant are a combination of outward and upward aspect.
*Flower persistent or self-cleaning.*—Persistent.
*Flower shape.*—Flower is calcarate in shape.
*Flower depth.*—Flower is 1 cm. in depth.
*Flower diameter.*—Flower is 1.50 cm. in diameter.
*Flower color.*—Flower color on an individual plant is a combination of individual colors 58B, 58C, 59A, and 5A.
*Petals.*—5 petals in number.
*Petal surface.*—Petal surface is glabrous.
*Petals fused or unfused.*—Petals are basally fused.
*Petal margin.*—Entire margin.
*Petal apex.*—Obtuse apex.
*Petal base.*—Rounded base.
*Petal shape.*—Petal shapes orbicular and reniform are individually present on an individual flower.
*Petal width.*—Petals that are 0.25 cm., 0.50 cm. and 1 cm. in width are individually present on an individual flower.
*Petal length.*—Petals that are 0.50 cm and 0.75 cm. in length are individually present on an individual flower.
*Petal color* (*abaxial surface*).—Petal is closest to 58C in color.
*Petal color* (*adaxial surface*).—Petal is closest to 58B in color.
*Corolla window color.*—Corolla window is 5A in color.
*Corolla window dimensions.*—Corolla window dimensions are 2 mm. in length and 2 mm. in width.
*Calcar.*—2 in number.
*Calcar surface.*—Calcar surface is glabrous.
*Calcar dimensions.*—Calcar is 6 mm. in depth and 2 mm. in diameter.
*Calcar color.*—Calcar is 59A in color.
*Bud shape.*—Bud is globose in shape.
*Bud surface.*—Bud surface is stipitate glandular.
*Bud color.*—Bud is 58D in color.
*Bud dimensions.*—Bud dimensions are 4 mm. in length and 4 mm. in width.
*Peduncle color.*—Peduncle is 178A in color.
*Peduncle dimensions.*—Peduncle dimensions are 1.50 cm. in length and 0.50 mm. in diameter.
*Peduncle shape.*—Peduncle is quadrilateral in shape.
*Peduncle surface.*—Peduncle surface is stipitate glandular.
*Pedicel color.*—Pedicel is 178A in color.
*Pedicel dimensions.*—Pedicel dimensions are 0.50 cm. in length and 0.25 mm. in width.
*Pedicel shape.*—Pedicel is cylindrical in shape.
*Pedicel surface.*—Pedicel surface is stipitate glandular.
*Calyx.*—Present.
*Calyx shape.*—Stelliform in shape.
*Calyx color.*—Calyx is 138A in color.
*Number of sepals.*—Five sepals in number.
*Sepals fused or unfused.*—Sepals are unfused.
*Sepal color* (*adaxial and abaxial surfaces*).—Sepal is 138A in color.
*Sepal surface.*—Sepal surface is stipitate glandular.
*Sepal shape.*—Sepal is closest to oblanceolate in shape.
*Sepal dimensions.*—Sepal dimensions are 4 mm. in length and 0.75 mm. in width.
*Sepal apex.*—Acute apex.
*Sepal base.*—Truncate base.
*Sepal margin.*—Entire margin.
*Blooming months.*—Flowers bloom April through November.
*Lastingness of flower on the plant.*—An individual flower lasts from 5 to 10 days.
*Flower fragrance.*—No fragrance is observed.

Reproductive organs:
*Stamens.*—4 stamens in number.
*Stamen color.*—Stamens are 59A in color.
*Stamen surface.*—Stamen surface is stipitate glandular.
*Stamen dimensions.*—Stamen dimensions are 4 mm. in length and 0.50 mm. in width.
*Anther dimensions.*—Anther dimensions are 2 mm. in length and 1 mm. in diameter.
*Anther shape.*—Globose in shape.
*Anther color.*—Anther is 5A in color.
*Quantity of pollen.*—Large amount of pollen observed.
*Color of pollen.*—Pollen is 5A in color.
*Pistil.*—One pistil in number.
*Pistil color.*—Pistil is 145A in color.
*Pistil surface.*—Pistil surface is stipitate glandular.
*Pistil dimensions.*—Pistil dimensions are 5 mm. in length and 0.50 mm. in width.
*Ovary position.*—Ovary is in superior position.
*Ovary color.*—Ovary is 145A in color.
*Ovary shape.*—Ovary is globose in shape.
*Ovary dimensions.*—Ovary dimensions are 2 mm. in height and 2 mm. in width.

Seed: 'PENDER' has not produced seed to date.

It is claimed:

1. A new and distinct cultivar of *Diascia* plant named 'PENDER' as described and illustrated herein.

* * * * *